United States Patent
Ukon et al.

(10) Patent No.: US 6,943,879 B2
(45) Date of Patent: Sep. 13, 2005

(54) METHOD FOR MONITORING AND/OR CONTROLLING THE STATUS OF A PLASMA IN A PLASMA SPECTROMETER AND SPECTROMETER FOR IMPLEMENTING SUCH A METHOD

(75) Inventors: Juichiro Ukon, Paris (FR); Yves Danthez, La Norville (FR)

(73) Assignee: Jobin Yvon, S.A., Longjumeau (FR)

( * ) Notice: Subject to any disclaimer, the term of this patent is extended or adjusted under 35 U.S.C. 154(b) by 518 days.

(21) Appl. No.: 09/986,656

(22) Filed: Nov. 9, 2001

(65) Prior Publication Data

US 2002/0071117 A1 Jun. 13, 2002

(30) Foreign Application Priority Data

Nov. 10, 2000 (FR) .......................................... 00 403139

(51) Int. Cl.[7] ................................................. G01J 3/30
(52) U.S. Cl. ....................................... 356/316; 356/326
(58) Field of Search .......................... 356/316; 250/288

(56) References Cited

U.S. PATENT DOCUMENTS

| | | | | |
|---|---|---|---|---|
| 4,820,046 A | * | 4/1989 | Sohma et al. ................ 356/328 |
| 5,050,992 A | * | 9/1991 | Drummond et al. ......... 356/328 |
| 5,474,642 A | * | 12/1995 | Zorina ......................... 156/345 |
| 5,489,820 A | * | 2/1996 | Ivanov et al. ........... 315/111.51 |
| 5,526,110 A | * | 6/1996 | Braymen .................... 356/316 |
| 5,642,190 A | * | 6/1997 | Krupa et al. ................. 356/316 |
| 6,213,050 B1 | * | 4/2001 | Liu et al. ................ 118/723 IR |
| 6,418,874 B1 | * | 7/2002 | Cox et al. .................. 118/723 I |
| 6,423,923 B1 | * | 7/2002 | Siniaguine ............. 219/121.59 |
| 6,462,300 B2 | * | 10/2002 | Siniaguine ............. 219/121.59 |
| 6,512,635 B1 | * | 1/2003 | Takeyama ................... 359/638 |
| 6,526,355 B1 | * | 2/2003 | Ni et al. ........................ 702/32 |

OTHER PUBLICATIONS

English translation of Japanese Patent Abstract, JP 07 085991 A, Mar. 31, 1995.

Ian I. Stewart et al., "Time–Resolved Measurements With Single Droplet Introduction To Investigate Space–Charge Effects In Plasma Mass Spectrometry", American Society for Mass Spectrometry, vol. 10, No. 2, Feb. 1999, pp. 159–174.

* cited by examiner

Primary Examiner—F. L. Evans
Assistant Examiner—Kara Geisel
(74) Attorney, Agent, or Firm—Arent Fox PLLC

(57) ABSTRACT

A method for monitoring and/or controlling the positioning and/or condition of a plasma in a plasma spectrometer, which comprises:
acquiring image data of the plasma through a video-camera (7), and
a) displaying on a display device (10) a plasma image from the acquired image data; and/or
b) storing the image data in a computer unit (9).

Figure 1:
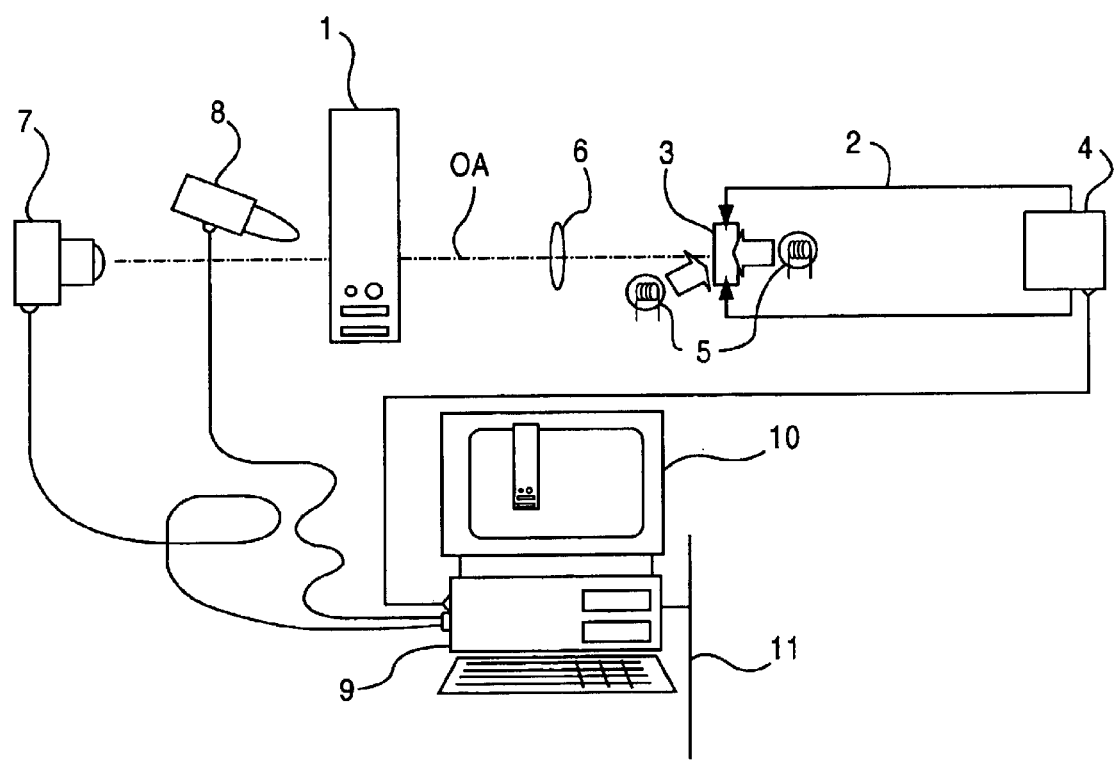

Application to inductively coupled high frequency plasma optical emission and mass spectrometers.

7 Claims, 2 Drawing Sheets

METHOD FOR MONITORING AND/OR CONTROLLING THE STATUS OF A PLASMA IN A PLASMA SPECTROMETER AND SPECTROMETER FOR IMPLEMENTING SUCH A METHOD

BACKGROUND OF THE INVENTION

The present invention relates to a method for monitoring and/or controlling the status of a plasma in a plasma-spectrometer such as a plasma-optical emission spectrometer or atomic spectrometer (ICP-OES or ICP-MS), and to spectrometer for implementing such a method.

It is a very common practice to analyse a material sample, using so-called "plasma-optical emission spectrometer" such as in particular inductively coupled high frequency plasma-optical emission spectrometers (ICP-OES) or atomic spectrometers such as a mass-spectrometer, in particular inductively coupled high frequency plasma mass spectrometer (ICP-MS).

In all these devices, there is obtained a plasma of the material sample to be analysed and either the light generated by the plasma or the chemical species formed in the plasma are analysed through an optical emission spectrometer or a mass spectrometer.

The accuracy of the analysis is highly dependent upon the plasma status and its generation conditions.

By the plasma status there is meant plasma physical characteristics such as the plasma position, in particular relative to a spectrometer entrance slit, plasma shape and/or contour, plasma intensity and/or color and in particular the position of the most intense portion of the plasma as well as the fluctuations of those characteristics.

In particular, the plasma position and the plasma shape and/or contour are or great influence onto the analytical performances of the spectrometer.

As long as those parameters are stable, the same performance can be obtained. However, those parameters are influenced by the plasma torch structure and the gas feeding rate. It means that, when the spectrometer is different, even of the same type and even with the same feeding conditions, the plasma characteristics may largely vary.

Presently, operators have to look at the plasma in the torch box, standing in front of the instrument when the conditions have changed, and usually visually determine whether the plasma is in optimal condition or not.

Also, the stability of the plasma influences the accuracy of the analysis data. Some spectrometers are equipped with means for showing the position of the torch mount which are associated with a scale or used with the motorized plasma torch holder. However, the scale or the position of the motorized holder does not always indicate the position of the plasma. Moreover, the fluctuation of the plasma torch cannot be monitored from the holder position. Thus, even though analysis data fluctuation can be estimated as being caused by plasma fluctuation, there is no evidence to show it.

As already indicated, the plasma position with regard to the spectrometer entrance slit deeply influences the performance of the analysis. Since up to now, there is no existing means for determining the spectrometer entrance slit position with regard to the plasma position, there is no possibility in the review of the analysis results to consider the position of the observation.

The shape of the plasma is affected by the gas feed condition and the torch structure.

The plasma shape also influences the analytical performances. The feeding gas conditions are often stored as the measurement conditions for later analysis with the same conditions or for later data review. However, when the plasma torch is replaced, it may happen that due to small changes of the torch structure the gas conditions are changed for optimisation. Since no record of the plasma image at the optimised conditions exist, there is no way for reproducing the former plasma conditions.

Finally, when the operators detect some troubles with the plasma such as fluctuation of the position or of the shape or generation of strange sounds, it is almost impossible to explain the situation to the manufacturer in the absence of any plasma image.

Thus, the aim of the present invention is to provide a method for monitoring and/or controlling the status of a plasma in a plasma-optical emission spectrometer or mass spectrometer which overcomes the drawbacks of the prior art.

The invention also concerns a plasma-spectrometer which incorporates means to implement the plasma status monitoring and/or controlling method.

The above goals are achieved according to the invention by providing a method for monitoring and/or controlling the status of a plasma in a plasma-spectrometer, which comprises:

acquiring image data of the plasma; and a) displaying an image of the plasma from the acquired image data on a display device, and/or b) storing the image data in a computer unit.

The spectrometer may be an optical emission spectrometer (OES) or a mass spectrometer (MS) and in particular an inductively coupled high frequency plasma optical emission spectrometer or mass spectrometer.

In a preferred embodiment of the process of the invention, the plasma sound is also recorded and monitored through the monitoring device and/or stored as sound data in the computer central unit.

With the present invention, the status of the plasma, such as plasma position, plasma shape and contour, plasma intensity and/or color can be monitored and displayed on line on the same monitoring device such as a monitor screen of the computer unit. Alternatively or simultaneously, the plasma image data can be stored and processed in the memory of the computer unit along with measured data. Processing of image data may comprise obtaining intensity images, intensity contour, color contour, intensity outline and time base fluctuation of image data. Then, the image data and the measured data of the plasma can be easily reviewed later on. In addition, the plasma image data and plasma measured data can be sent to remote places so that the plasma can be monitored from a remote site.

This would be also the case for the recording of the plasma sound. The image data can also be processed through the computer unit for establishing an optimal data set. For example, the image data can be processed to get the most intense position within the plasma using the outline shape, and the intensity, the colour analysis and the light intensity analysis such as the contour of the plasma.

The method of the present invention allows an online continuous monitoring and/or storing of the analysis results. Therefore, the fluctuation of the plasma image characteristics based on the image analysis such as the most intense position fluctuation or the plasma shape fluctuation can be calculated and displayed and/or stored. Similarly, the plasma sound, once recorded, can be, if necessary processed for example to determine frequency distribution or the time domain frequency distribution changes.

All this information can be used by the operator either immediately to determine whether or not the plasma is in requisite conditions for normal analysis or later on to set up optimal plasma conditions.

When the spectrometer is an optical emission spectrometer, as it is well known, the plasma may be placed in two different orientations with regard to the spectrometer optical axis. These orientations are usually referred as radial plasma and axial plasma. Radial plasma means that the plasma is vertically oriented with regard to the spectrometer optical axis and is observed in a lateral direction by the spectrometer detector device. In other words, the optical axis of the spectrometer and in fact of the spectrometer detector device is perpendicular to the plasma orientation.

On the other hand, axial plasma means that the plasma is horizontally oriented and is observed by the spectrometer detector device in the axial direction. In other words, the plasma is axially oriented along the optical axis of the spectrometer detector device.

In the case of a radial plasma in which the plasma is vertically oriented with regard to the optical axis of the spectrometer, imaging of the plasma is effected in register with the optical axis, for example by placing a video-camera in alignment with the spectrometer optical axis. The plasma is then positioned at the focal point of the video-camera. In that case, the entrance slit of the detector device of the spectrometer is also viewed by the video-camera and can be imaged by the video-camera simultaneously with the plasma. In that later case, the entrance slit of the spectrometer detector device is focused at the plasma and is also placed at a focal point of the video-camera.

Preferably, for a better imaging, the entrance slit can be illuminated. The illumination of the entrance slit can be made from the outside or the inside, for example by using lamps inside or outside of the monochromer of the spectrometer detector device.

With an axial plasma, imaging of the plasma is effected in a direction perpendicular to the optical axis of the spectrometer detector device.

In that case of course, an imaging of the entrance slit of the spectrometer detector device is obviously not possible.

This is in particular the case when the spectrometer is a mass-spectrometer wherein the chemical species generated in the plasma must entered the detector device.

As indicated previously, recording of the plasma sound can be made by a microphone disposed and fixed in the plasma enclosure. The microphone may be placed in any position within the enclosure wherein a good recording a the plasma sound can be obtained. In particular, the microphone may eventually be incorporated with the video-camera.

The invention also concerns a plasma spectrometer for implementing the above described method which comprises a video-camera fixed on an enclosure for the plasma, preferably an inductively coupled high frequency plasma, which is coupled to a display device and/or a computer unit for imaging the plasma and/or storing plasma image data.

Depending upon the fact that the plasma in the spectrometer would be a radial plasma or an axial plasma, the video camera would be axially or perpendicularly oriented with regard to the optical axis of the spectrometer. However, the camera optical axis is always perpendicular to the plasma axis. In the case of a radial plasma spectrometer and with the video-camera axially positioned on the optical axis of the spectrometer, there is then a possibility of imaging simultaneously the plasma and the entrance slit of the spectrometer.

Since in such a case the entrance slit and the plasma are placed in register positions, a slit image can, therefore, be observed and recorded. When the plasma is turned on, the slit position in the plasma can then be seen by superimposing the recorded image of the entrance slit on the monitored plasma image, thereby ensuring the analysis position in the plasma. Obviously, the superimposed images can also be recorded as analytical data for further data review.

The plasma position and the plasma shape influence the analytical performances of the spectrometer. As long as those parameters are stable, the same performances can be obtained. However, those parameters are influenced by the plasma torch structure and the gas feeding rate.

When the spectrometer is a different one, even of the same type, and even with the same feeding conditions, the plasma characteristics are not always similar. With the method and spectrometer according to the invention, image data of the plasma can be displayed and/or stored. This provides a possible comparison between two different plasma images or plasma image data. Therefore, after having recorded the best image or the best image data for the plasma and when the plasma torch is replaced or when other instruments are installed on the spectrometer, the new setting parameters can be obtained easily so that they reproduce the same plasma shape, contour, intensity and position according to the optimal image characteristics displayed or recorded.

The same holds true for the recording of the plasma sound.

Figure 2:
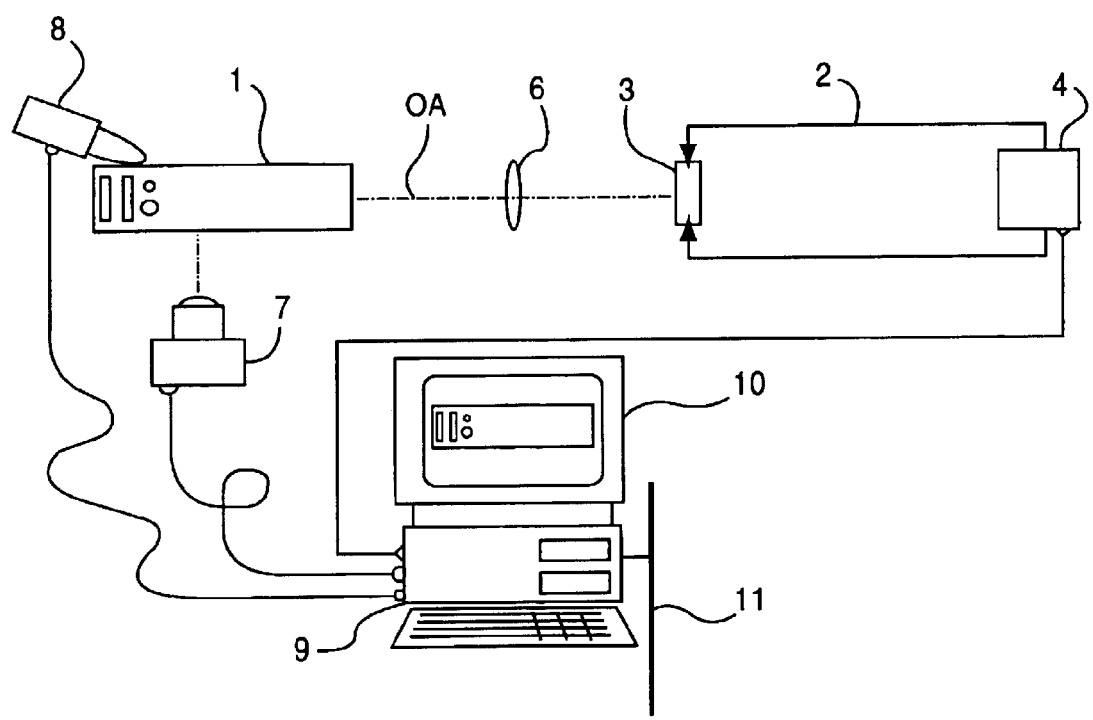

The invention will now be described in connection with the figures which schematically represent, respectively:

FIG. 1: an inductively coupled high frequency plasma-optical emission spectrometer of the radial type according to the invention;

FIG. 2: an inductively coupled high frequency plasma-optical emission or mass spectrometer of the axial type, according to the invention.

Referring to FIG. 1, there is represented schematically an inductively coupled high frequency plasma-optical emission spectrometer according to the invention. The spectrometer as typically comprises a plasma generating device 1 and a detector device 2 comprising an entrance slit 3 optically coupled with a detector 4. The spectrometer represented on FIG. 1 is of the radial plasma type, that is the plasma generated in the plasma device 1 is oriented perpendicularly to the optical axis (OA) of the spectrometer detector device. As usual, the detector device is focused on the plasma 1. Typically, a relay lens 6 is placed between the plasma and the entrance slit 3 of the detector device 2. According to the invention, a video-camera 7 is fixed to the plasma device enclosure, so that the lens of the camera is aligned with the optical axis OA of the spectrometer detector device, so that the plasma 1 is at a focal point of the video-camera 7. With such a configuration, the video-camera 7 is able to image both the plasma and the entrance slit 3 of the spectrometer detector device 2.

In order to improve imaging of the entrance slit 3 of the spectrometer detector device 2, a lamp 5 may be placed either inside or outside of the detector device, in order to illuminate the entrance slit 3. Also, a microphone 8 is fixed to the enclosure of the plasma generating device 1 in a position allowing recording of the plasma sound. Both video-camera 7 and a microphone 8 are connected to a computer unit 9 and through this computer unit 9 to a display device 10 such as a monitoring screen. Possibly, the computer unit 9 may be connected to a local data network through lines 11.

The spectrometer just described allows to acquire image data and to display the image on the monitor as well as to process the image data through the computer unit 9. Image data can also be recorded and stored in the computer unit 9 where they can be retrieved and eventually processed when necessary along with a spectral or analytical data. These image data can also be transferred to other computers through the local network.

The just disclosed spectrometer allows to acquire image data both from the plasma and from the entrance slit 3 of the detector device 2 of the spectrometer.

There is represented on FIG. 2 an inductively coupled high frequency plasma-optical emission spectrometer of the axial type according to the invention.

This spectrometer of the axial type is essentially similar to the spectrometer described in connection with FIG. 1 except that the plasma generated by the plasma device 1 is axially oriented with regard to the optical axis OA of the spectrometer detector device 2 and the video-camera 7 is fixed on the enclosure of the plasma generating device 1 in a perpendicular direction to the optical axis of the spectrometer detector device 2. Of course, the video-camera 7 is placed in the enclosure so that the plasma is positioned at a focal point of the video-camera 7.

Obviously, with such a radial plasma spectrometer, the video camera is not able to image the spectrometer detector device entrance slit 3. Otherwise, this embodiment would function and perform as the embodiment of FIG. 1.

The axial position of the plasma in the embodiment of FIG. 2 allows replacing the optical emission spectrometer by a mass spectrometer. In that case, relay lens 6 as well as the entrance slit 3 would be replaced by the diaphragm of the mass spectrometer. Otherwise, functioning and results would be similar.

What is claimed is:

1. A method for monitoring and/or controlling the status of a radially oriented plasma in an optical emission plasma spectrometer, said spectrometer having an entrance slit, which comprises the steps of:
    acquiring image data associated with the plasma;
    acquiring image data associated with the entrance slit; and at least one of:
        a) displaying simultaneously, on a display device, each of an image of the plasma from the image data associated with the plasma and an image of the entrance slit from the image data associated with the entrance slit; and
        b) storing simultaneously, in a computer unit, each of the image data associated with the plasma, the image data associated with the entrance slit, and measured data.

2. The method according to claim 1, further comprising the steps of:
    processing the image data associated with the plasma to obtain at least one of an intensity image, an intensity contour, a color contour, an intensity outline, and time based fluctuations of the image data associated with the plasma; and
    comparing the measured data with a plasma optimal condition data set.

3. The method according to claim 2, further comprising the step of positioning at least one of the display device and the computer unit remotely from the spectrometer.

4. The method according to claim 2, further comprising the steps of:
    acquiring plasma sound data; and at least one of:
        reproducing plasma sound from the plasma sound data on the display; and
        storing the plasma sound data in the computer unit.

5. An optical emission plasma spectrometer comprising a video-camera fixed to an enclosure of a plasma generating device, wherein the video-camera is coupled to at least one of a display device and a computer unit, the plasma is radially oriented with respect to an optical axis of the plasma spectrometer, and the video-camera is axially positioned with respect to the optical axis of the spectrometer so that the video-camera is configured to simultaneously obtain image data of an entrance slit of the spectrometer and image data of the plasma.

6. The optical emission spectrometer according to claim 5, further comprising a lamp positioned in the vicinity of the entrance slit, wherein the lamp is configured to illuminate the entrance slit.

7. The optical emission spectrometer according to claim 5, further comprising a microphone fixed to the enclosure of the plasma generating device, wherein the microphone is configured to obtain plasma sound data, and the microphone is coupled to the computer unit for storing the plasma sound data or processing the plasma sound data, or both.

* * * * *